United States Patent [19]

Nguyen et al.

[11] Patent Number: 5,861,497
[45] Date of Patent: *Jan. 19, 1999

[54] TRABECULAR MESHWORK INDUCED GLUCOCORTICOID RESPONSE (TIGR) NUCLEIC ACID MOLECULES

[75] Inventors: Thai D. Nguyen; Jon R. Polansky, both of Mill Valley; Weidong Huang, San Francisco, all of Calif.

[73] Assignee: The Regents of the University of California, Oakland, Calif.

[ * ] Notice: The term of this patent shall not extend beyond the expiration date of Pat. No. 5,606,043.

[21] Appl. No.: 667,790

[22] Filed: Jun. 21, 1996

Related U.S. Application Data

[62] Division of Ser. No. 336,235, Nov. 3, 1994, Pat. No. 5,606,043.

[51] Int. Cl.⁶ .............................. C12N 15/11; C12N 15/12
[52] U.S. Cl. ...................... 536/23.5; 536/23.1; 536/24.33
[58] Field of Search ................................. 536/23.5, 24.33, 536/23.1

[56] References Cited

U.S. PATENT DOCUMENTS

| | | | |
|---|---|---|---|
| 4,617,299 | 10/1986 | Knepper | 514/178 |
| 4,757,089 | 7/1988 | Epstein | 514/571 |
| 4,829,088 | 5/1989 | Doulakas, Jr. | 514/567 |
| 5,124,154 | 6/1992 | Babcock et al. | 424/427 |
| 5,130,238 | 7/1992 | Malek et al. . | |
| 5,169,766 | 12/1992 | Schuster et al. . | |
| 5,192,535 | 3/1993 | Davis et al. | 424/78.04 |
| 5,420,120 | 5/1995 | Boltralik | 514/172 |
| 5,474,985 | 12/1995 | Polansy et al. | 514/26 |
| 5,606,043 | 2/1997 | Nguyen et al. | 536/23.5 |

FOREIGN PATENT DOCUMENTS

| | | |
|---|---|---|
| O 329 822 A2 | 8/1989 | European Pat. Off. . |
| WO 88/10315 | 12/1988 | WIPO . |
| WO 89/06700 | 7/1989 | WIPO . |
| WO89/06964 | 8/1989 | WIPO . |
| WO 90/01069 | 2/1990 | WIPO . |
| 96/14411 | 5/1996 | WIPO . |

OTHER PUBLICATIONS

Polansky, J.R. et al, "Glucocorticoid Receptors and Steroid Glaucoma Mechanisms," In Encounters in Glaucoma Research 1:Receptor Biology and Glaucoma, Fogliazza Editore, Milan pp. 273–299 (1994).

Polansky, J.R. et al, "Cellular Mechanisms Influencing the Aqueous Outflow Pathway," In: Principles and Practice of Ophthalmology, Albert, D.M et al., Eds., .B. Saunders & Co. Philadelphia, pp. 226–251 (1994).

Polansky, J.R., "HTM Cell Culture Model for Steroid Effects on Intraocular Pressue: Overview," In: Schriftenreihe de Adaddemie der Wissenschaften un der Literatur, Mainz, 307–318 (1993).

Nguyen, T. D. et al, "Glucocorticoid (GC) Effects on HTM Cells: Molecular Biology Approaches," In: Schriftenreihe de Adademie der Wissenschaften und der Literatur Mainz, 331–343 (1993).

Polansky, J.R., "Growth Factor Efects and Modulation of Glucocorticoid (GC) and other Stress Responses in Human Trabecular Meshwork (HTM) Cells," *Exper. Eye Res.* 55:Ab265 (1992).

Clark, A.F., "Evaluation of Anti–Glaucoma Compounds and Discovery of Pathogenic Mechanisms using Perfusion Cultured Human Eyes," *Exper. Eye Res.* 55:Ab266 (1992).

Vaughan, D. et al., In: *General Ophthalmology,* Appelton & Lange, Norwalk, CT, pp. 213–230 (1992)).

Zhan, G.L. et al., "Steroid Glaucoma: Corticosteroid–Induced Ocular Hypertension in Cats," *Exper. Eye Res.* 54:211–218 (1992).

Nguyen, T. D. et al. "Molecular Biology Studies of Steroid–Induced Glaucoma Model Using Cultured Human Trabecular Meshwork," *Invest Opthtalmol* Vis. Sci. 32789 (1991).

Polansky, J.R. et al., "In Vitro Correlates of Glucocorticoid Effects on Intraocular Pressue," In: *Glaucoma Update IV,* Springer–Verlag, Berlin, pp. 20–29 (1991).

Fauss et al., "Comparisons of Glucocorticoid (GC) Effects and Oxidative Stress on Protein/Glycoprotein Synthesis in Cultured Cells", Invest. Opthamol. Visual Sci. 31(4): 435 (1990).

Yun, A.J. et al., "Proteins Secreted By Human Trabecular Cells," *Invest. Ophthalmol. Vis. Sci.* 30:2012–2022 (1989).

Polansky, J.R. et al, "Eicosanoid Production and Glucocorticoid Regulatory Mechanisms in Cultured Human Trabecular Meshwork Cels," *Prog Clin Biol Res* 312:113–138 (1989).

Partridge et al. "Dexamethasone Induces Specific Ptoteins in Human Trabecular Meshwork Cells". Invest. Opthamol. Visual Sci. 30(8): 1843–1847 (1989).

Weinreb, R.N. et al., Detection of Glucocorticoid Receptors in Cultured Human Trabecular Cells, *Invest Ophthalmol. Vis. Sci.* 21:403–407 (1981).

Polansky, J.R. et al., "Studies on Human Trabecular Cells Propagated In Vitro," *Vision Research,* 21:155–160 (1981).

Nguyen et al "Cloning of glucocorticoid–induced proteins in HTM cells: verification of progressive, high dose dependent cDNAs to correlate with effects on IOP" *Invest. Opthalmol. Vis, Sci.* 31:789 (1990).

Stone et al., "Identification of a Gene that Causes Primary Open Angle Glaucoma", *Science* 275:668–670 (1997).

Chen et al. Expression of Trabecular Meshwork Inducible Glucocorticoid Response (TIGR) peptide in Sf9 cells. Investigative Opthalmology & Visual Science. vol. 34, No. 4, p. 1385, May 15, 1993.

Sambrook et al. Molecular Cloning, 2d Edition, CSHL Press, Cold Spring Harbor, New York. Chapters 9 and 11, 1989.

(List continued on next page.)

*Primary Examiner*—Elizabeth Kemmerer
*Attorney, Agent, or Firm*—Howrey & Simon

[57] ABSTRACT

A glucocorticoid-induced protein, TIGR, that is produced by cells of the trabecular meshwork can be used to diagnose glaucoma. The TIGR protein, anti-TIGR antibodies, and TIGR encoding sequences also provide a diagnostic for glaucoma and its related diseases.

6 Claims, 4 Drawing Sheets

OTHER PUBLICATIONS

Walker, G.T. et al., *Proc. Natl. Acad. Sci. (U.S.A.)* 89:392–396 (1992).

Barany, Francis, "Genetic Disease Detection And DNA Amplification Using Cloned Thermostble Ligase," *Proc. Natl. Acad. Sci. U.S.A.*, 88:189–193 (1991).

Nickerson, Deborah A., et al., "Automated DNA Diagnostics Using An ELISA–Based Oligonucleotide Ligation Assay," *Proc. Natl. Acad. Sci. U.S.A.*, 87:8923–8927 (1990).

Kwoh, D.Y., et al., "Transcription–Based Amplification System and Detection of Amplified Human Immunodeficiency Virus Type 1 With a Bead–Based Sandwhich Hybridization Format," *Proc. Natl. Acad. Sci. U.S.A.*, 86:1173–1177 (1989).

Rychlik, W., et al., "A Computer Program for Choosing Optimal Oligonucleotides for Filter Hybridization, Sequencingand In vitro Amplification of DNA," Nucleic Acids Res., 17:8543–8551 (1989).

Baldino, F. et al., "High–Resolution in Situ Hybridization Histochemistry," Meth. Enzymol., 168:761–777 (1989).

Landergren, Ulf, et al., "A Ligase–Mediated Gene Detection Technique," Science 241:1017–1080 (1988).

Breslauer, K.J., et al., "Predicting DNA Duplex Stability from the Base Sequence," Proc. Natl. Acad. Sci., U.S.A., 83:3746–3750 (1986).

Freier, S.M., et al., "Improved Free–Energy Parameters for Predictions of RNA Duplex Stability," Proc. Natl. Acad. Sci., U.S.A., 83:9373–9377 (1986).

Wu, D.Y. et al., Genomics 4:560 (1989).

Lathe, R., Synthetic Oligonucleotide Probes deduced from Amino Acid Sequence Data. Theoretical and Practical Considerations, J. Mol. Biol. 183:1–12 (1985).

Schildkraut, C., et al., Dependence of the Melting Temperature of DNA on Salt Concentration, Biopolymers 3:195–208 91965).

```
-1                      -21                       -41
AGAGCTTTCC  AGAGGAAGCC  TGACCAAGCC  TCTGCA  ATG AGG TTC TTC
                                            met arg phe phe
            -61                       -81
TGT GCA CGT TGC TGC AGC TTT GGG CCT GAG ATG CCA GCT GTC CAG
cys ala arg cys cys ser phe gly pro glu met pro ala val gln
            -101                      -121
CTG CTG CTT CTG GCC TGC CTG GTG TGG GAT GTG GGG GCC AGG ACA
leu leu leu leu ala cys leu val trp asp val gly ala arg thr
     -141                      -161                      -181
GCT CAG CTC AGG AAG GCC AAT GAC CAG AGT GGC CGA TGC CAG TAT
ala gln leu arg lys ala asn asp gln ser gly arg cys gln tyr
                     -201                      -221
ACC TTC AGT GTG GCC AGT CCC AAT GAA TCC AGC TGC CCA GAG CAG
thr phe ser val ala ser pro asn glu ser ser cys pro glu gln
            -241                      -261
AGC CAG GCC ATG TCA GTC ATC CAT AAC TTA CAG AGA GAC AGC AGC
ser gln ala met ser val ile his asn leu gln arg asp ser ser
            -281                      -301
ACC CAA CGC TTA GAC CTG GAG GCC ACC AAA GCT CGA CTC AGC TCC
thr gln arg leu asp leu glu ala thr lys ala arg leu ser ser
     -321                      -341                      -361
CTG GAG AGC CTC CTC CAC CAA TTG ACC TTG GAC CAG GCT GCC AGG
leu glu ser leu leu his gln leu thr leu asp gln ala ala arg
                     -381                      -401
CCC CAG GAG ACC CAG GAG GGG CTG CAG AGG GAG CTG GGC ACC CTG
pro gln glu thr gln glu gly leu gln arg glu leu gly thr leu
            -421                      -441
AGG CGG GAG CGG GAC CAG CTG GAA ACC CAA ACC AGA GAG TTG GAG
arg arg glu arg asp gln leu glu thr gln thr arg glu leu glu
```

FIG. 1A

```
           -461                         -481
ACT GCC TAC AGC AAC CTC CTC CGA GAC AAG TCA GTT CTG GAG GAA
thr ala tyr ser asn leu leu arg asp lys ser val leu glu glu
   -501                        -521                       -541
GAG AAG AAG CGA CTA AGG CAA GAA AAT GAG AAT CTG GCC AGG AGG
glu lys lys arg leu arg gln glu asn glu asn leu ala arg arg
                          -561                       -581
TTG GAA AGC AGC AGC CAG GAG GTA GCA AGG CTG AGA AGG GGC CAG
leu glu ser ser ser gln glu val ala arg leu arg arg gly gln
                      -601                    -621
TGT CCC CAG ACC CGA GAC ACT GCT CGG GCT GTG CCA CCA GGC TCC
cys pro gln thr arg asp thr ala arg ala val pro pro gly ser
           -641                        -661
AGA GAA GTT TCT ACG TGG AAT TTG GAC ACT TTG GCC TTC CAG GAA
arg glu val ser thr trp asn leu asp thr leu ala phe gln glu
   -681                        -701                       -721
CTG AAG TCC GAG CTA ACT GAA GTT CCT GCT TCC CGA ATT TTG AAG
leu lys ser glu leu thr glu val pro ala ser arg ile leu lys
                          -741                       -761
GAG AGC CCA TCT GGC TAT CTC AGG AGT GGA GAG GGA GAC ACC GGA
glu ser pro ser gly tyr leu arg ser gly glu gly asp thr gly
                      -781                    -801
TGT GGA GAA CTA GTT TGG GTA GGA GAG CCT CTC ACG CTG AGA ACA
cys gly glu leu val trp val gly glu pro leu thr leu arg thr
                  -821                      -841
GCA GAA ACA ATT ACT GGC AAG TAT GGT GTG TGG ATG CGA GAC CCC
ala glu thr ile thr gly lys tyr gly val trp met arg asp pro
```

FIG. 1B

```
                    -861                         -881                         -901
           AAG CCC ACC TAC CCC TAC ACC CAG GAG ACC ACG TGG AGA ATC GAC
           lys pro thr tyr pro tyr thr gln glu thr thr trp arg ile asp
                                        -921                         -941
           ACA GTT GGC ACG GAT GTC CGC CAG GTT TTT GAG TAT GAC CTC ATC
           thr val gly thr asp val arg gln val phe glu tyr asp leu ile
                                        -961                         -981
           AGC CAG TTT ATG CAG GGC TAC CCT TCT AAG GTT CAC ATA CTG CCT
           ser gln phe met gln gly tyr pro ser lys val his ile leu pro
                                       -1001                        -1021
           AGG CCA CTG GAA AGC ACG GGT GCT GTG GTG TAC TCG GGG AGC CTC
           arg pro leu glu ser thr gly ala val val tyr ser gly ser leu
                   -1041                        -1061                        -1081
           TAT TTC CAG GGC GCT GAG TCC AGA ACT GTC ATA AGA TAT GAG CTG
           tyr phe gln gly ala glu ser arg thr val ile arg tyr glu leu
                                       -1101                        -1121
           AAT ACC GAG ACA GTG AAG GCT GAG AAG GAA ATC CCT GGA GCT GGC
           asn thr glu thr val lys ala glu lys glu ile pro gly ala gly
                                       -1141                        -1161
           TAC CAC GGA CAG TTC CCG TAT TCT TGG GGT GGC TAC ACG GAC ATT
           tyr his gly gln phe pro tyr ser trp gly gly tyr thr asp ile
                   -1181                        -1201
           GAC TTG GCT GTG GAT GAA GCA GGC CTC TGG GTC ATT TAC AGC ACC
           asp leu ala val asp glu ala gly leu trp val ile tyr ser thr
                  -1221                         -1241                        -1261
           GAT GAG GCC AAA GGT GCC ATT GTC CTC TCC AAA CTG AAC CCA GAG
           asp glu ala lys gly ala ile val leu ser lys leu asn pro glu
                                       -1281                        -1301
           AAT CTG GAA CTC GAA CAA ACC TGG GAG ACA AAC ATC CGT AAG CAG
           asn leu glu leu glu gln thr trp glu thr asn ile arg lys gln
```

FIG. 1C

```
              -1321                    -1341
TCA GTC GCC AAT GCC TTC ATC ATC TGT GGC ACC TTG TAC ACC GTC
ser val ala asn ala phe ile ile cys gly thr leu tyr thr val
        -1361                   -1381
AGC AGC TAC ACC TCA GCA GAT GCT ACC GTC AAC TTT GCT TAT GAC
ser ser tyr thr ser ala asp ala thr val asn phe ala tyr asp
  -1401                     -1421                      -1441
ACA GGC ACA GGT ATC AGC AAG ACC CTG ACC ATC CCA TTC AAG AAC
thr gly thr gly ile ser lys thr leu thr ile pro phe lys asn
                      -1461                 -1481
CGC TAT AAG TAC AGC AGC ATG ATT GAC TAC AAC CCC CTG GAG AAG
arg tyr lys tyr ser ser met ile asp tyr asn pro leu glu lys
              -1501                  -1521
AAG CTC TTT GCC TGG GAC AAC TTG AAC ATG GTC ACT TAT GAC ATC
lys leu phe ala trp asp asn leu asn met val thr tyr asp ile
            -1541                  -1561
AAG CTC TCC AAG ATG TGA AAAGCCTCC AAGCTGTACA GGCAATGGCA
lys leu ser lys met
-1581              -1601          -1621
GAAGGAGATG CTCAGGGCTC CTGGGGGGAG CAGGCTGAAG GGAGAGCCAG
              -1641          -1661
CCAGCCAGGG CCCAGGCAGC TTTGACTGCT TTCCAAGTTT TCATTAATCC
-1681              -1701          -1721
AGAAGGATGA ACATGGTCAC CATCTAACTA TTCAGGAATT GTAGTCTGAG
              -1741          -1761
GGCGTAGACA ATTTCATATA ATAAATATCC TTTATCTTCT GTCAGCATTT
-1781              -1801          -1821
ATGGGATGTT TAATGACATA GTTCAAGTTT TCTTGTGATT TGGGGCAAAA
              -1841          -1861
GCTGTAAGGC ATAATAGTTT CTTCCTGAAA ACCATTGCTC TTGCATGTTA
-1881              -1901          -1921
CATGGTTACC ACAAGCCACA ATAAAAAGCA TAACTTCTAA AGGAAGCAGA
              -1941          -1961
ATAGCTCCTC TGGCCAGCAT CGAATATAAG TAAGATGCAT TTACTACAGT
-1981
TGGCTTCTAA TGCTTCAGA
```

FIG. 1D

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 504 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:1:

```
Met  Arg  Phe  Phe  Cys  Ala  Arg  Cys  Cys  Ser  Phe  Gly  Pro  Glu  Met  Pro
 1              5                        10                       15

Ala  Val  Gln  Leu  Leu  Leu  Leu  Ala  Cys  Leu  Val  Trp  Asp  Val  Gly  Ala
              20                        25                       30

Arg  Thr  Ala  Gln  Leu  Arg  Lys  Ala  Asn  Asp  Gln  Ser  Gly  Arg  Cys  Gln
           35                      40                  45

Tyr  Thr  Phe  Ser  Val  Ala  Ser  Pro  Asn  Glu  Ser  Ser  Cys  Pro  Glu  Gln
     50                      55                       60

Ser  Gln  Ala  Met  Ser  Val  Ile  His  Asn  Leu  Gln  Arg  Asp  Ser  Ser  Thr
65                        70                  75                           80

Gln  Arg  Leu  Asp  Leu  Glu  Ala  Thr  Lys  Ala  Arg  Leu  Ser  Ser  Leu  Glu
                    85                       90                       95

Ser  Leu  Leu  His  Gln  Leu  Thr  Leu  Asp  Gln  Ala  Ala  Arg  Pro  Gln  Glu
                100                      105                     110

Thr  Gln  Glu  Gly  Leu  Gln  Arg  Glu  Leu  Gly  Thr  Leu  Arg  Arg  Glu  Arg
          115                      120                     125

Asp  Gln  Leu  Glu  Thr  Gln  Thr  Arg  Glu  Leu  Glu  Thr  Ala  Tyr  Ser  Asn
     130                      135                     140

Leu  Leu  Arg  Asp  Lys  Ser  Val  Leu  Glu  Glu  Glu  Lys  Lys  Arg  Leu  Arg
145                      150                     155                      160

Gln  Glu  Asn  Glu  Asn  Leu  Ala  Arg  Arg  Leu  Glu  Ser  Ser  Ser  Gln  Glu
                165                      170                     175
```

| | | | | | | | | | | | | | | |
|---|---|---|---|---|---|---|---|---|---|---|---|---|---|---|
| Val | Ala | Arg | Leu<br>180 | Arg | Arg | Gly | Gln | Cys<br>185 | Pro | Gln | Thr | Arg | Asp<br>190 | Thr | Ala |
| Arg | Ala | Val<br>195 | Pro | Pro | Gly | Ser | Arg<br>200 | Glu | Val | Ser | Thr<br>205 | Trp | Asn | Leu | Asp |
| Thr | Leu<br>210 | Ala | Phe | Gln | Glu<br>215 | Leu | Lys | Ser | Glu | Leu<br>220 | Glu | Val | Pro | Ala |
| Ser<br>225 | Arg | Ile | Leu | Lys | Glu<br>230 | Ser | Pro | Ser | Gly<br>235 | Tyr | Leu | Arg | Ser | Gly | Glu<br>240 |
| Gly | Asp | Thr | Gly | Cys<br>245 | Gly | Glu | Leu | Val | Trp<br>250 | Val | Gly | Glu | Pro | Leu<br>255 | Thr |
| Leu | Arg | Thr | Ala<br>260 | Glu | Thr | Ile | Thr | Gly<br>265 | Lys | Tyr | Gly | Val | Trp<br>270 | Met | Arg |
| Asp | Pro | Lys<br>275 | Pro | Thr | Tyr | Pro | Tyr<br>280 | Thr | Gln | Glu | Thr | Thr<br>285 | Trp | Arg | Ile |
| Asp | Thr<br>290 | Val | Gly | Thr | Asp | Val<br>295 | Arg | Gln | Val | Phe | Glu<br>300 | Tyr | Asp | Leu | Ile |
| Ser<br>305 | Gln | Phe | Met | Gln | Gly<br>310 | Tyr | Pro | Ser | Lys | Val<br>315 | His | Ile | Leu | Pro | Arg<br>320 |
| Pro | Leu | Glu | Ser | Thr<br>325 | Gly | Ala | Val | Val | Tyr<br>330 | Ser | Gly | Ser | Leu | Tyr<br>335 | Phe |
| Gln | Gly | Ala | Glu<br>340 | Ser | Arg | Thr | Val | Ile<br>345 | Arg | Tyr | Glu | Leu | Asn<br>350 | Thr | Glu |
| Thr | Val | Lys<br>355 | Ala | Glu | Lys | Glu | Ile<br>360 | Pro | Gly | Ala | Gly | Tyr<br>365 | His | Gly | Gln |
| Phe | Pro<br>370 | Tyr | Ser | Trp | Gly | Gly<br>375 | Tyr | Thr | Asp | Ile | Asp<br>380 | Leu | Ala | Val | Asp |
| Glu<br>385 | Ala | Gly | Leu | Trp | Val<br>390 | Ile | Tyr | Ser | Thr | Asp<br>395 | Glu | Ala | Lys | Gly | Ala<br>400 |
| Ile | Val | Leu | Ser | Lys<br>405 | Leu | Asn | Pro | Glu | Asn<br>410 | Leu | Glu | Leu | Glu | Gln<br>415 | Thr |
| Trp | Glu | Thr | Asn<br>420 | Ile | Arg | Lys | Gln | Ser<br>425 | Val | Ala | Asn | Ala | Phe<br>430 | Ile | Ile |
| Cys | Gly | Thr<br>435 | Leu | Tyr | Thr | Val | Ser<br>440 | Ser | Tyr | Thr | Ser | Ala<br>445 | Asp | Ala | Thr |
| Val | Asn<br>450 | Phe | Ala | Tyr | Asp | Thr<br>455 | Gly | Thr | Gly | Ile | Ser<br>460 | Lys | Thr | Leu | Thr |
| Ile<br>465 | Pro | Phe | Lys | Asn | Arg<br>470 | Tyr | Lys | Tyr | Ser | Ser<br>475 | Met | Ile | Asp | Tyr | Asn<br>480 |
| Pro | Leu | Glu | Lys | Lys<br>485 | Leu | Phe | Ala | Trp | Asp<br>490 | Asn | Leu | Asn | Met | Val<br>495 | Thr |
| Tyr | Asp | Ile | Lys | Leu<br>500 | Ser | Lys | Met | | | | | | | | |

( 2 ) INFORMATION FOR SEQ ID NO:2:

( i ) SEQUENCE CHARACTERISTICS:
        ( A ) LENGTH: 1999 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
AGAGCTTTCC AGAGGAAGCC TCACCAAGCC TCTGCAATGA GGTTCTTCTG TGCACGTTGC      60
TGCAGCTTTG GGCCTGAGAT GCCAGCTGTC CAGCTGCTGC TTCTGGCCTG CCTGGTGTGG     120
```

```
GATGTGGGGG  CCAGGACAGC  TCAGCTCAGG  AAGGCCAATG  ACCAGAGTGG  CCGATGCCAG    180

TATACCTTCA  GTGTGGCCAG  TCCCAATGAA  TCCAGCTGCC  CAGAGCAGAG  CCAGGCCATG    240

TCAGTCATCC  ATAACTTACA  GAGAGACAGC  AGCACCCAAC  GCTTAGACCT  GGAGGCCACC    300

AAAGCTCGAC  TCAGCTCCCT  GGAGAGCCTC  CTCCACCAAT  TGACCTTGGA  CCAGGCTGCC    360

AGGCCCCAGG  AGACCCAGGA  GGGGCTGCAG  AGGGAGCTGG  GCACCCTGAG  GCGGGAGCGG    420

GACCAGCTGG  AAACCCAAAC  CAGAGAGTTG  GAGACTGCCT  ACAGCAACCT  CCTCCGAGAC    480

AAGTCAGTTC  TGGAGGAAGA  GAAGAAGCGA  CTAAGGCAAG  AAAATGAGAA  TCTGGCCAGG    540

AGGTTGGAAA  GCAGCAGCCA  GGAGGTAGCA  AGGCTGAGAA  GGGGCCAGTG  TCCCCAGACC    600

CGAGACACTG  CTCGGGCTGT  GCCACCAGGC  TCCAGAGAAG  TTTCTACGTG  GAATTTGGAC    660

ACTTTGGCCT  TCCAGGAACT  GAAGTCCGAG  CTAACTGAAG  TTCCTGCTTC  CCGAATTTTG    720

AAGGAGAGCC  CATCTGGCTA  TCTCAGGAGT  GGAGAGGGAG  ACACCGGATG  TGGAGAACTA    780

GTTTGGGTAG  GAGAGCCTCT  CACGCTGAGA  ACAGCAGAAA  CAATTACTGG  CAAGTATGGT    840

GTGTGGATGC  GAGACCCCAA  GCCCACCTAC  CCCTACACCC  AGGAGACCAC  GTGGAGAATC    900

GACACAGTTG  GCACGGATGT  CCGCCAGGTT  TTTGAGTATG  ACCTCATCAG  CCAGTTTATG    960

CAGGGCTACC  CTTCTAAGGT  TCACATACTG  CCTAGGCCAC  TGGAAAGCAC  GGGTGCTGTG   1020

GTGTACTCGG  GGAGCCTCTA  TTTCCAGGGC  GCTGAGTCCA  GAACTGTCAT  AAGATATGAG   1080

CTGAATACCG  AGACAGTGAA  GGCTGAGAAG  GAAATCCCTG  GAGCTGGCTA  CCACGGACAG   1140

TTCCCGTATT  CTTGGGGTGG  CTACACGGAC  ATTGACTTGG  CTGTGGATGA  AGCAGGCCTC   1200

TGGGTCATTT  ACAGCACCGA  TGAGGCCAAA  GGTGCCATTG  TCCTCTCCAA  ACTGAACCCA   1260

GAGAATCTGG  AACTCGAACA  AACCTGGGAG  ACAAACATCC  GTAAGCAGTC  AGTCGCCAAT   1320

GCCTTCATCA  TCTGTGGCAC  CTTGTACACC  GTCAGCAGCT  ACACCTCAGC  AGATGCTACC   1380

GTCAACTTTG  CTTATGACAC  AGGCACAGGT  ATCAGCAAGA  CCCTGACCAT  CCCATTCAAG   1440

AACCGCTATA  AGTACAGCAG  CATGATTGAC  TACAACCCCC  TGGAGAAGAA  GCTCTTTGCC   1500

TGGGACAACT  TGAACATGGT  CACTTATGAC  ATCAAGCTCT  CCAAGATGTG  AAAAGCCTCC   1560

AAGCTGTACA  GGCAATGGCA  GAAGGAGATG  CTCAGGGCTC  CTGGGGGAG   CAGGCTGAAG   1620

GGAGAGCCAG  CCAGCCAGGG  CCCAGGCAGC  TTTGACTGCT  TTCCAAGTTT  TCATTAATCC   1680

AGAAGGATGA  ACATGGTCAC  CATCTAACTA  TTCAGGAATT  GTAGTCTGAG  GGCGTAGACA   1740

ATTTCATATA  ATAAATATCC  TTTATCTTCT  GTCAGCATTT  ATGGGATGTT  TAATGACATA   1800

GTTCAAGTTT  TCTTGTGATT  TGGGGCAAAA  GCTGTAAGGC  ATAATAGTTT  CTTCCTGAAA   1860

ACCATTGCTC  TTGCATGTTA  CATGGTTACC  ACAAGCCACA  ATAAAAGCA   TAACTTCTAA   1920

AGGAAGCAGA  ATAGCTCCTC  TGGCCAGCAT  CGAATATAAG  TAAGATGCAT  TTACTACAGT   1980

TGGCTTCTAA  TGCTTCAGA                                                    1999
```

( 2 ) INFORMATION FOR SEQ ID NO:3:

( i ) SEQUENCE CHARACTERISTICS:
        ( A ) LENGTH: 1512 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
ATGAGGTTCT  TCTGTGCACG  TTGCTGCAGC  TTTGGGCCTG  AGATGCCAGC  TGTCCAGCTG     60

CTGCTTCTGG  CCTGCCTGGT  GTGGGATGTG  GGGGCCAGGA  CAGCTCAGCT  CAGGAAGGCC    120
```

-continued

| | | | | | | |
|---|---|---|---|---|---|---|
|AATGACCAGA|GTGGCCGATG|CCAGTATACC|TTCAGTGTGG|CCAGTCCCAA|TGAATCCAGC|180|
|TGCCCAGAGC|AGAGCCAGGC|CATGTCAGTC|ATCCATAACT|TACAGAGAGA|CAGCAGCACC|240|
|CAACGCTTAG|ACCTGGAGGC|CACCAAAGCT|CGACTCAGCT|CCCTGGAGAG|CCTCCTCCAC|300|
|CAATTGACCT|TGGACCAGGC|TGCCAGGCCC|CAGGAGACCC|AGGAGGGGCT|GCAGAGGGAG|360|
|CTGGGCACCC|TGAGGCGGGA|GCGGGACCAG|CTGGAAACCC|AAACCAGAGA|GTTGGAGACT|420|
|GCCTACAGCA|ACCTCCTCCG|AGACAAGTCA|GTTCTGGAGG|AAGAGAAGAA|GCGACTAAGG|480|
|CAAGAAAATG|AGAATCTGGC|CAGGAGGTTG|GAAAGCAGCA|GCCAGGAGGT|AGCAAGGCTG|540|
|AGAAGGGGCC|AGTGTCCCCA|GACCCGAGAC|ACTGCTCGGG|CTGTGCCACC|AGGCTCCAGA|600|
|GAAGTTTCTA|CGTGGAATTT|GGACACTTTG|GCCTTCCAGG|AACTGAAGTC|CGAGCTAACT|660|
|GAAGTTCCTG|CTTCCCGAAT|TTTGAAGGAG|AGCCCATCTG|GCTATCTCAG|GAGTGGAGAG|720|
|GGAGACACCG|GATGTGGAGA|ACTAGTTTGG|GTAGGAGAGC|CTCTCACGCT|GAGAACAGCA|780|
|GAAACAATTA|CTGGCAAGTA|TGGTGTGTGG|ATGCGAGACC|CCAAGCCCAC|CTACCCCTAC|840|
|ACCCAGGAGA|CCACGTGGAG|AATCGACACA|GTTGGCACGG|ATGTCCGCCA|GGTTTTGAG|900|
|TATGACCTCA|TCAGCCAGTT|TATGCAGGGC|TACCCTTCTA|AGGTTCACAT|ACTGCCTAGG|960|
|CCACTGGAAA|GCACGGGTGC|TGTGGTGTAC|TCGGGGAGCC|TCTATTTCCA|GGGCGCTGAG|1020|
|TCCAGAACTG|TCATAAGATA|TGAGCTGAAT|ACCGAGACAG|TGAAGGCTGA|GAAGGAAATC|1080|
|CCTGGAGCTG|GCTACCACGG|ACAGTTCCCG|TATTCTTGGG|GTGGCTACAC|GGACATTGAC|1140|
|TTGGCTGTGG|ATGAAGCAGG|CCTCTGGGTC|ATTTACAGCA|CCGATGAGGC|CAAAGGTGCC|1200|
|ATTGTCCTCT|CCAAACTGAA|CCCAGAGAAT|CTGGAACTCG|AACAAACCTG|GGAGACAAAC|1260|
|ATCCGTAAGC|AGTCAGTCGC|CAATGCCTTC|ATCATCTGTG|GCACCTTGTA|CACCGTCAGC|1320|
|AGCTACACCT|CAGCAGATGC|TACCGTCAAC|TTTGCTTATG|ACACAGGCAC|AGGTATCAGC|1380|
|AAGACCCTGA|CCATCCCATT|CAAGAACCGC|TATAAGTACA|GCAGCATGAT|TGACTACAAC|1440|
|CCCCTGGAGA|AGAAGCTCTT|TGCCTGGGAC|AACTTGAACA|TGGTCACTTA|TGACATCAAG|1500|
|CTCTCCAAGA|TG| | | | |1512|

TRABECULAR MESHWORK INDUCED GLUCOCORTICOID RESPONSE (TIGR) NUCLEIC ACID MOLECULES

This application is a continuation division of application Ser. No. 08/366,235 filed Nov. 3, 1994, now U.S. Pat. No. 5,606,043.

FIELD OF THE INVENTION

The present invention is in the fields of diagnostics, and concerns methods and reagents for diagnosing glaucoma and related disorders. This invention was supported with Government funds (NIH EY02477 and NIH EY 08905-02). The Government has certain rights in this invention.

BACKGROUND OF THE INVENTION

"Glaucomas" are a group of debilitating eye diseases that are the leading cause of preventable blindness in the United States and other developed nations. Primary Open Angle Glaucoma ("POAG") is the most common form of glaucoma. The disease is characterized by the degeneration of the trabecular meshwork, leading to obstruction of the normal ability of aqueous humor to leave the eye without closure of the space (e.g., the "angle") between the iris and cornea (see, Vaughan, D. et al., In: *General Ophthamology*, Appleton & Lange, Norwalk, Conn., pp. 213–230 (1992)). A characteristic of such obstruction in this disease is an increased intraocular pressure ("IOP"), resulting in progressive visual loss and blindness if not treated appropriately and in a timely fashion.

The disease is estimated to affect between 0.4% and 3.3% of all adults over 40 years old (Leske, M. C. et al., *Amer. J. Epidemiol.* 113:1843–1846 (1986); Bengtsson, B., *Br. J. Ophthamol.* 73:483–487 (1989); Strong, N. P., *Ophthal. Physiol. Opt.* 12:3–7 (1992)). Moreover, the prevalence of the disease rises with age to over 6% of those 75 years or older (Strong, N. P., *Ophthal. Physiol. Opt.* 12:3–7 (1992)).

A link between the IOP response of patients to glucocorticoids and the disease of POAG has long been suspected. While only 5% of the normal population shows a high IOP increase (16 mm Hg) to topical glucocorticoid testing, over 90% of patients with POAG show this response. In addition, an open angle glaucoma may be induced by exposure to glucocorticoids. This observation has suggested that an increased or abnormal glucocorticoid response in trabecular cells may be involved in POAG (Zhan, G. L. et al., *Exper. Eye Res.* 54:211–218 (1992); Yun, A. J. et al., *Invest. Ophthamol. Vis. Sci.* 30:2012–2022 (1989); Clark, A. F., *Exper. Eye Res.* 55:265 (1992); Klemetti, A., *Acta Ophthamol.* 68:29–33 (1990); Knepper, P. A., U.S. Pat. No. 4,617,299).

The ability of glucocorticoids to induce a glaucoma-like condition has led to efforts to identify genes or gene products that would be induced by the cells of the trabecular meshwork in response to glucocorticoids (Polansky, J. R. et al., In: *Glaucoma Update* IV, Springer-Verlag, Berlin, pp. 20–29 (1991)). Initial efforts using short-term exposure to dexamethasone revealed only changes in specific protein synthesis. Extended exposure to relatively high levels of dexamethasone was, however, found to induce the expression of related 66 kD and 55 kD proteins that could be visualized by gel electrophoresis (Polansky, J. R. et al, In: *Glaucoma Update* IV, Springer-Verlag, Berlin, pp.20–29 (1991)). The induction kinetics of these proteins as well as their dose response characteristics were similar to the kinetics those that were required for steroid-induced IOP elevation in human subjects (Polansky, J. R. et al., In: *Glaucoma Update* IV, Springer-Verlag, Berlin, pp. 20–29 (1991)). Problems of aggregation and apparent instability or loss of protein in the purification process were obstacles in obtaining a direct protein sequence.

Because increased IOP is a readily measurable characteristic of glaucoma, the diagnosis of the disease is largely screened for by measuring intraocular pressure (tonometry) (Strong, N. P., *Ophthal. Physiol. Opt.* 12:3–7 (1992), Greve, M. et al., *Can. J. Ophthamol.* 28:201–206 (1993)). Unfortunately, because glaucomatous and normal pressure ranges overlap, such methods are of limited value unless multiple readings are obtained (Hitchings, R. A., *Br. J. Ophthamol.* 77:326 (1993); Tuck, M. W. et al., *Ophthal. Physiol. Opt.* 13:227–232 (1993); Vaughan, D. et al., In: *General Ophthamology*, Appleton & Lange, Norwalk, Conn., pp. 213–230 (1992); Vernon, S. A., *Eye* 7:134–137 (1993)). For this reason, additional methods, such as direct examination of the optic disk and determination of the extent of a patient's visual field loss are often conducted to improve the accuracy of diagnosis (Greve, M. et al., *Can. J. Ophthamol.* 28:201–206 (1993)).

In view of the importance of glaucoma, and the at least partial inadequacies of prior methods of diagnosis, it would be desirable to have an improved, more accurate method for diagnosing glaucoma. The present invention provides such improved diagnostic agents and methods.

SUMMARY OF THE INVENTION

The invention concerns a novel peptide sequence discovered to be highly induced by glucocorticoids in the endothelial lining cells of the human trabecular meshwork. The cDNA for this protein, the protein itself, molecules that bind to it, and nucleic acid molecules that encode it, provide improved methods and reagents for diagnosing glaucoma and related disorders, as well as for diagnosing other diseases or conditions, such as cardiovascular, immunological, or other diseases or conditions that affect the expression or activity of the protein. Indeed, the molecules of the present invention may be used to diagnose diseases or conditions which are characterized by alterations in the expression of extracellular proteins. In addition, due to its cellular functions and DNA binding properties, the molecules of the present invention may be used to diagnose diseases or conditions which are characterized those functions.

The clone was termed "II.2" during the procedures of its isolation and was subsequently renamed "TIGR" ("Trabecular Meshwork Induced Glucocorticoid Response") protein.

In detail, the invention provides a substantially purified TIGR protein having the sequence of SEQ ID NO:1 residues 1–497 or 15–197.

The invention further provides a nucleic acid molecule that encodes a TIGR protein, especially a nucleic acid molecule that comprises the sequence of SEQ ID NO:2 or SEQ ID NO:3.

The invention also provides an antibody capable of specifically binding to a TIGR protein.

The invention also provides a method for diagnosing glaucoma in a patient which comprises determining whether the amount of a TIGR protein present in the trabecular meshwork of an eye of the patient exceeds the amount of that TIGR protein present in the trabecular meshwork of an eye of an individual who is not suffering from glaucoma, wherein the detection of an excessive amount of the TIGR protein is indicative of glaucoma.

The invention also provides a method for quantitatively or qualitatively determining the amount of a TIGR protein present in the trabecular meshwork of an eye of an individual, and determining whether that amount exceeds the amount of that TIGR protein present in the trabecular meshwork of an eye of an individual who is not suffering from glaucoma, wherein the detection of an excessive amount of the TIGR protein is indicative of glaucoma.

BRIEF DESCRIPTION OF THE FIGURE

FIGS. 1A–1D provide the amino acid sequence of the TIGR protein and the sequence of the cDNA that encodes the TIGR protein (SEQ ID NO:1, SEQ ID NO:2 and SEQ ID NO:3).

DETAILED DESCRIPTION OF THE INVENTION

I. Overview of the Invention

As indicated above, the trabecular meshwork has been proposed to play an important role in the normal flow of the aqueous, and has been presumed to be the major site of outflow resistance in glaucomatous eyes. Human trabecular meshwork (HTM) cells are endothelial like cells which line the outflow channels by which aqueous humor exits the eye; altered synthetic function of the cells may involve in the pathogenesis of steroid glaucoma and other types of glaucoma. Sustained steroid treatment of these cells are interesting because it showed major difference was observed when compared to 1–2 day glucocorticoid (GC) exposure, which appears relevant to the clinical onset of steroid glaucoma (1–6 weeks).

Despite decades of research, prior to the present invention, the molecular basis for glaucoma had not been determined (Snyder, R. W. et al., *Exper. Eye Res.* 57:461–468 (1993); Wiggs, J. L. et al., *Genomics* 21:299–303 (1994)).

Although trabecular meshwork cells had been found to induce specific proteins in response to glucocorticoids (see, Polansky, J. R., In: "*Schriftenreihe de Adademie der Wissenschaften und der Literatur, Mainz,*" 307–318 (1993)), efforts to purify the expressed protein were encumbered by insolubility and other problems. Nguyen, T. D. et al. (In: "*Schriftenreihe de Adademie der Wissenschaften und der Literatur, Mainz,*" 331–343 (1993), herein incorporated by reference) used a molecular cloning approach to isolate a highly induced mRNA species from glucocorticoid-induced human trabecular cells. The mRNA exhibited a time course of induction that was similar to the glucocorticoid-induced proteins. The clone was designated "II.2" (ATCC No. 97994, deposited on Apr. 18, 1997, American Type Culture Collection, 10801 University Boulevard, Manassas, Va. 20110-2209.

The present invention stems in part from the recognition that the isolated II.2 clone encodes a novel secretory protein (termed "Trabecular Meshwork Induced Glucocorticoid Response" protein or "TIGR") that is induced in cells of the trabecular meshwork upon exposure to glucocorticoids. It has been proposed that this protein may become deposited in the extracellular spaces of the trabecular meshwork and bind to the surface of the endothelial cells that line the trabecular meshwork, thus causing a decrease in aqueous flow. Quantitative dot blot analysis and PCR evaluations have shown that the TIGR mRNA exhibits a progressive induction with time whereas other known GC-inductions from other systems and found in HTM cells (metallothionein, alpha-1 acid glycoprotein and alpha-1 antichymotrypsin) reached maximum level at one day or earlier. Of particular interest, the induction level of this clone was very high (4–6% total cellular mRNA) and with control level undetectable without PCR method. Based on studies of $^{35}$S methionine cell labeling, the clone has the characteristics recently discovered for the major GC-induced extracellular blycoprotein in these cells, which is a sialenated, N-glycosylated molecule with a putative inositol phosphate anchor. The induction of TIGR RNA approached 4% of the total cellular mRNA. The mRNA increased progressively over 10 days of dexamethasone treatment.

The II.2 clone is 2.0 Kb whereas the Northern blotting shows a band of 2.5 Kb. Although not including a poly A tail, the 3' end of the clone contains two consensus polyadenylation signals. Southern analysis suggested two groups of genomic sequences and two genomic clones were isolated. In-situ hybridization using this genomic probe showing the gene locations on chromosome 1, p36 and 12, p13, p15. Study of cyclohexamide treatment in the absence and presence of GC suggest that the induction of TIGR may involve factors in addition to the GC receptor. The TIGR gene may be involved in the cellular stress response since it is also induced by stimulants such as $H_2O_2$, TPA, glucose and heat; this fact may relate to glaucoma pathogenesis and treatment.

The amino acid sequence of TIGR, the cDNA sequence that encodes TIGR, and the 2.0 kb nucleotide sequence that contains this coding region are shown in FIGS. 1A–1D. The amino acid sequence of TIGR is shown in FIGS. 1A–1D (and in SEQ ID NO:1). The nucleotide sequence of SEQ ID NO:2 is that of the TIGR cDNA molecule that is shown in FIGS. 1A–1D. The portion of SEQ ID NO:2 that is shown in FIGS. 1A–1D as encoding the TIGR protein is presented as SEQ ID NO:3.

The primary structure of TIGR initiates from an ATG initiation site (SEQ ID NO:2, residue 1) and includes a 20 amino acid consensus signal sequence at a second ATG (SEQ ID NO:2, residue 15), indicating that the protein is a secretory protein. The protein contains an N-linked glycosylation site located in the most hydrophilic region of the molecule. The amino terminal portion of the protein is highly polarized and adopts alpha helical structure as shown by its hydropathy profile and the Garnier-Robison structure analysis. In contrast, the protein contains a 25 amino acid hydrophobic region near its carboxy terminus. This region may comprise a GIP anchoring sequence. Thus, the invention concerns two TIGR proteins: TIGR and a processed form of TIGR.

The TIGR protein also contains 5 putative O-linked glycosylation sites throughout the molecule. "Leucine zipper" regions define a helical structure that permits protein-protein binding to occur (see, generally, Tso, J. Y. et al., PCT Patent Application WO93/11162; Land, K. H. et al., PCT Patent Application WO93/19176). The TIGR protein contain 7 leucine zipper units. The presence of the zipper regions provides a means for the TIGR molecules to bind to one another forming macromolecular and possible aggregation. Studies showing the specific binding of this molecule to HTM cells (but not to fibroblast cells) support the notion that it can influence the outflow pathway in HTM tissue to cause the increased intra-ocular pressure that characterizes glaucoma and its related diseases. TIGR protein has also been successfully expressed using the baculovirus system and Sf9 insect cells. The major recombinant proteins are the two 55 kd cellular proteins encoded by the TIGR cDNA. Antibodies produced from these protein recognize both the cellular 55 kD proteins and the secreted 66 kD glycosylated form of these proteins in dexamethasome-treated HTM cells and in organ culture systems. In situ analysis of glaucomatous tissue specimens show a high expression level of this protein relative to normal controls.

The presence, induction, and level of the TIGR secretory protein mirror the onset and kinetics with which glucocorticoids induce glaucoma, and the glucocorticoid-induced expression of this secretory protein comprises the molecular basis for glaucoma and its related diseases. Such an understanding of the molecular basis permits the definition of diagnostic agents for glaucoma and its related diseases.

II. The Preferred Agents of the Invention

As used herein, the term "glaucoma" has its art recognized meaning, and includes both primary glaucomas, secondary glaucomas, and familial (i.e. inherited glaucomas). The methods of the present invention are particularly relevant to the diagnosis of POAG, OAG, juvenile glaucoma, and inherited glaucomas. A disease or condition is said to be related to glaucoma if it possesses or exhibits a symptom of glaucoma, for example, an increased intraocular pressure resulting from aqueous outflow resistance (see, Vaughan, D. et al., In: *General Ophthamology*, Appleton & Lange, Norwalk, Conn., pp. 213–230 (1992)). The preferred agents of the present invention are discussed in detail below.

The agents of the present invention are capable of being used to diagnose the presence or severity of glaucoma and itsrelated diseases in a patient suffering from glaucoma (a "glaucomatous patient"). Such agents may be either naturally occurring or non-naturally occurring. As used herein, a naturally occurring molecule may be "substantially purified," if desired, such that one or more molecules that is or may be present in a naturally occurring preparation containing that molecule will have been removed or will be present at a lower concentration than that at which it would normally be found.

The agents of the present invention will preferably be "biologically active" with respect to either a structural attribute, such as the capacity of a nucleic acid to hybridize to another nucleic acid molecule, or the ability of a protein to be bound by antibody (or to compete with another molecule for such binding) Alternatively, such an attribute may be catalytic, and thus involve the capacity of the agent to mediate a chemical reaction or response.

The agents of the present invention comprise nucleic acid molecules, proteins, and organic molecules.

A. Nucleic Acid Molecules

A preferred class of agents of the present invention comprises TIGR nucleic acid molecules ("TIGR molecules"). Such molecules may be either DNA or RNA.

In one embodiment, such nucleic acid molecules will encode all or a fragment of TIGR protein, its "promoter" or flanking gene sequences. As used herein, the term "promoter" is used in an expansive sense to refer to the regulatory sequence(s) that control mRNA production. Such sequences include RNA polymerase binding sites, glucocorticoid response elements, enhancers, etc. All such TIGR molecules may be used to diagnose the presence of glaucoma and severity of glaucoma.

Fragment TIGR nucleic acid molecules may encode significant portion(s) of, or indeed most of, the TIGR protein. Alternatively, the fragments may comprise smaller oligonucleotides (having from about 15 to about 250 nucleotide residues, and more preferably, about 15 to about 30 nucleotide residues.). Such oligonucleotides may be used as probes of TIGR mRNA. For such purpose, the oligonucleotides must be capable of specifically hybridizing to a TIGR nucleic acid molecule. As used herein, two nucleic acid molecules are said to be capable of specifically hybridizing to one another if the two molecules are capable of forming an anti-parallel, double-stranded nucleic acid structure, whereas they are unable to form a double-stranded structure when incubated with a non-TIGR nucleic acid molecule. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook, J., et al., (In: *Molecular Cloning, a Laboratory Manual, 2nd Edition*, Cold Spring Harbor Press, Cold Spring Harbor, N.Y. (1989)), and by Haymes, B. D., et al. (In: *Nucleic Acid Hybridization, A Practical Approach*, IRL Press, Washington, D.C. (1985)), both herein incorporated by reference). Departures from complete complementarity are therefore permissible, as long as such departures do not completely preclude the capacity of the molecules to form a double-stranded structure. Thus, in order for an oligonucleotide to serve as a primer it need only be sufficiently complementary in sequence to be able to form a stable double-stranded structure under the particular solvent and salt concentrations employed.

Apart from their diagnostic uses, such oligonucleotides may be employed to obtain other TIGR nucleic acid molecules. Such molecules include the TIGR-encoding nucleic acid molecule of non-human animals (particularly, cats, monkeys, rodents and dogs), fragments thereof, as well as their promoters and flanking sequences. Such molecules can be readily obtained by using the above-described primers to screen cDNA or genomic libraries obtained from non-human species. Methods for forming such libraries are well known in the art. Such analogs may differ in their nucleotide sequences from that of SEQ ID NO:1, because complete complementarity is not needed for stable hybridization. The TIGR nucleic acid molecules of the present invention therefore also include molecules that, although capable of specifically hybridizing with TIGR nucleic acid molecules may lack "complete complementarity."

Any of a variety of methods may be used to obtain the above-described nucleic acid molecules. SEQ ID NO:2 may be used to synthesize all or any portion of the TIGR protein or the TIGR cDNA (Zamechik et al., *Proc. Natl. Acad. Sci. (U.S.A.)* 83:4143 (1986); Goodchild et al., *Proc. Natl. Acad. Sci. (U.S.A.)* 85:5507 (1988); Wickstrom et al., *Proc. Natl. Acad. Sci. (U.S.A.)* 85:1028; Holt, J. T. et al., *Molec. Cell. Biol.* 8:963 (1988); Gerwirtz, A. M. et al., *Science* 242:1303 (1988); Anfossi, G., et al., *Proc. Natl. Acad. Sci. (U.S.A.)* 86:3379 (1989); Becker, D., et al., *EMBO J.* 8:3679 (1989); all of which references are incorporated herein by reference). Automated nucleic acid synthesizers may be employed for this purpose. In lieu of such synthesis, the disclosed SEQ ID NO:2 may be used to define a pair of primers that can be used with the polymerase chain reaction (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194)) to amplify and obtain any desired TIGR-encoding DNA molecule or fragment.

The TIGR promoter sequence(s) and TIGR flanking sequences can also be obtained using the SEQ ID NO:2 sequence provided herein. In one embodiment, such sequences are obtained by incubating oligonucleotide probes of TIGR oligonucleotides with members of genomic human libraries and recovering clones that hybridize to the probes. In a second embodiment, methods of "chromosome walking," or 3' or 5' RACE may be used (Frohman, M. A. et al., *Proc. Natl. Acad. Sci.* (*U.S.A.*) 85:8998–9002 (1988); Ohara, O. et al., *Proc. Natl. Acad. Sci.* (*U.S.A.*) 86:5673–5677 (1989)) to obtain such sequences.

B. TIGR Protein and Peptide Molecules

A second preferred class of agents ("TIGR molecules") comprises the TIGR protein, its peptide fragments, fusion proteins, and analogs. As used herein, the term "TIGR protein" refers to a protein having the amino acid sequence of SEQ ID NO:1. TIGR protein may be produced via chemical synthesis, or more preferably, by expressing TIGR-encoding cDNA in a suitable bacterial or eukaryotic host. Most preferably, the subsequence of such cDNA that encodes TIGR may be used for this purpose (SEQ ID NO:3). Alternatively, the entire SEQ ID NO:2 shown in FIGS. 1A–1D may be employed. Suitable methods for expression are described by Sambrook, J., et al., (In: *Molecular Cloning, a Laboratory Manual, 2nd Edition*, Cold Spring Harbor Press, Cold Spring Harbor, N.Y. (1989)), or similar texts.

A "TIGR fragment" is a peptide or polypeptide whose amino acid sequence comprises a subset of the amino acid sequence of TIGR protein. A TIGR protein or fragment thereof that comprises one or more additional non-TIGR peptide regions is a "TIGR fusion" protein. Such molecules may be derivatized to contain carbohydrate or other moieties (such as keyhole limpet hemocyanin, etc.). As in the case of TIGR protein, the fragments and fusions of the present invention are preferably produced via recombinant means.

The analogs of the TIGR molecules comprise TIGR proteins, fragments or fusions in which non-essential, or nor relevant, amino acid residues have been added, replaced, or deleted. An example of such an analog is the TIGR protein of non-human species, such as primates, dogs, cats, etc. Such analogs can readily be obtained by any of a variety of methods. Most preferably, as indicated above, the disclosed SEQ ID NO:2 will be used to define a pair of primers that may be used to isolate the TIGR-encoding nucleic acid molecules from any desired species. Such molecules can be expressed to yield TIGR analogs by recombinant means.

C. Antibodies Reactive Against TIGR

One aspect of the present invention concerns antibodies, single-chain antigen binding molecules, or other proteins that specifically bind to TIGR protein and its analogs, fusions or fragments. Such antibodies are "anti-TIGR antibodies," and may be used to diagnose glaucoma and its related diseases. As used herein, an antibody or peptide is said to "specifically bind" to TIGR if such binding is not competitively inhibited by the presence of non-TIGR molecules.

Nucleic acid molecules that encode all or part of the TIGR protein can be expressed, via recombinant means, to yield TIGR protein or peptides that can in turn be used to elicit antibodies that are capable of binding TIGR. Such antibodies may be used in immunodiagnostic assays of glaucoma. Such TIGR-encoding molecules, or their fragments may be a "fusion" molecule (i.e. a part of a larger nucleic acid molecule) such that, upon expression, a fusion protein is produced.

The antibodies that specifically bind TIGR proteins and protein fragments may be polyclonal or monoclonal, and may comprise intact immunoglobulins, of antigen binding portions of immunoglobulins (such as (F(ab'), F(ab')$_2$) fragments, or single-chain immunoglobulins producible, for example, via recombinant means.

Murine monoclonal antibodies are particularly preferred. BALB/c mice are preferred for this purpose, however, equivalent strains may also be used. The animals are preferably immunized with approximately 25 µg of purified TIGR protein (or fragment thereof) that has been emulsified a suitable adjuvant (such as TiterMax adjuvant (Vaxcel, Norcross, Ga.)). Immunization is preferably conducted at two intramuscular sites, one intraperitoneal site, and one subcutaneous site at the base of the tail. An additional i.v. injection of approximately 25 µg of antigen is preferably given in normal saline three weeks later. After approximately 11 days following the second injection, the mice may be bled and the blood screened for the presence of anti-TIGR antibodies. Preferably, a direct binding ELISA is employed for this purpose.

Most preferably, the mouse having the highest antibody titer is given a third i.v. injection of approximately 25 µg of TIGR protein or fragment. The splenic leukocytes from this animal may be recovered 3 days later, and are then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs") to TIGR protein, preferably by direct ELISA.

In one embodiment, anti-TIGR monoclonal antibodies are isolated using TIGR fusions, or conjugates, as immunogens. Thus, for example, a group of mice can be immunized using a TIGR fusion protein emulsified in Freund's complete adjuvant (approximately 50 µg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding TIGR at 1:5,000 dilution can also be obtained using this method.

In a preferred procedure for obtaining monoclonal antibodies, the spleens of the above-described immunized mice are removed, disrupted, and immune splenocytes are isolated over a ficoll gradient. The isolated splenocytes are fused, using polyethylene glycol with BALB/c-derived HGPRT (hypoxanthine guanine phosphoribosyl transferase) deficient P3x63xAg8.653 plasmacytoma cells. The fused cells are plated into 96 well microtiter plates and screened for hybridoma fusion cells by their capacity to grow in culture medium supplemented with hypothanthine, aminopterin and thymidine for approximately 2–3 weeks. On average, out of every $10^6$ spleen cells subjected to fusion yields a viable hybridoma. A typical spleen yields 5–10×$10^7$ spleen cells.

Hybridoma cells that arise from such incubation are preferably screened for their capacity to produce an immunoglobulin that binds to TIGR protein. An indirect ELISA may be used for this purpose. In brief, the supernatants of hybridomas are incubated in microtiter wells that contain immobilized TIGR protein. After washing, the titer of bound immunoglobulin can be determined using, for example, a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbors. Desirably, the fusion plates are screened several times since the rates of hybridoma growth vary. In a preferred sub-embodiment, a different antigenic form of TIGR may be used to screen the hybridoma. Thus, for example, the splenocytes may be immunized with one TIGR immunogen, but the resulting hybridomas can be screened using a different TIGR immunogen.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as fluorescent group, a radioisotope or an enzyme).

The ability to produce antibodies that bind TIGR molecules permits the identification of mimetic compounds of TIGR. A "mimetic compound" of TIGR is a compound that is not TIGR, or a fragment of TIGR, but which nonetheless exhibits an ability to specifically bind to anti-TIGR antibodies. Such molecules can be used to elicit anti-TIGR antibodies, and thus, may be used to assist the diagnosis of glaucoma and its related diseases.

III. Uses of the Molecules of the Invention in the Diagnosis of Glaucoma and Related Diseases A particularly desired use of the present invention relates to the diagnosis of glaucoma and its related diseases. As indicated above, methods for diagnosing glaucoma suffer from inaccuracy, or require multiple examinations. The molecules of the present invention may be used to define superior assays for glaucoma.

In a first embodiment, the TIGR molecules of the present invention are used to determine whether an individual has a mutation in the TIGR gene, or in regulatory regions or other genes that control or affect the expression of TIGR, in order to identify individuals who would be predisposed to glaucoma and related diseases.

In one sub-embodiment, such an analysis is conducted by determining the presence and/or identity of polymorphisms in the TIGR gene or its flanking regions which are associated with glaucoma, or a predisposition to glaucoma. The genomes of animals and plants naturally undergo spontaneous mutation in the course of their continuing evolution (Gusella, J. F., *Ann. Rev. Biochem.* 55:831–854 (1986)).

A "polymorphism" in the TIGR gene or its flanking regions is a variation or difference in the sequence of the TIGR gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e. the original "allele") whereas other members may have the variant sequence (i.e. the variant "allele"). In the simplest case, only one variant sequence may exist, and the polymorphism is thus said to be di-allelic. In other cases, the species' population may contain multiple alleles, and the polymorphism is termed tri-allelic, etc. A single gene may have multiple different unrelated polymorphisms. For example, it may have a di-allelic polymorphism at one site, and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity and paternity analysis (Weber, J. L., U.S. Pat. No. 5,075,217; Armour, J. A. L. et al., *FEBS* Lett. 307:113–115 (1992); Jones, L. et al.,*Eur. J. Haematol.* 39:144–147 (1987); Horn, G. T. et al., PCT Application WO91/14003; Jeffreys, A. J., European Patent Application 370,719; Jeffreys, A. J., U.S. Pat. No. 5,175,082); Jeffreys. A. J. et al., *Amer. J. Hum. Genet.* 39:11–24 (1986); Jeffreys. A. J. et al., *Nature* 316:76–79 (1985); Gray, I. C. et al., *Proc. R. Acad. Soc. Lond.* 243:241–253 (1991); Moore, S. S. et al., *Genomics* 10:654–660 (1991); Jeffreys, A. J. et al., *Anim. Genet.* 18:1–15 (1987); Hillel, J. et al., *Anim. Genet.* 20:145–155 (1989); Hillel, J. et al., *Genet.* 124:783–789 (1990)).

The identification of a polymorphism in the TIGR gene can be determined in a variety of ways. By correlating the presence or absence of glaucoma in an individual with the presence or absence of a polymorphism in the TIGR gene or its flanking regions, it is possible to diagnose the predisposition of an asymptomatic patient to glaucoma. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and animal genetic analyses (Glassberg, J., UK patent Application 2135774; Skolnick, M. H. et al., *Cytogen. Cell Genet.* 32:58–67 (1982); Botstein, D. et al., *Ann. J. Hum. Genet.* 32:314–331 (1980); Fischer, S. G et al. (PCT Application WO90/13668); Uhlen, M., PCT Application WO90/11369)). The role of TIGR in glaucoma pathogenesis indicates that genetic alterations (e.g., DNA polymorphisms) are associated with the TIGR gene.

In accordance with this embodiment of the invention, a sample DNA is obtained from a patient's cells. In a preferred embodiment, the DNA sample is obtained from the patient's blood. However, any source of DNA may be used. The DNA is subjected to restriction endonuclease digestion. TIGR is used as a probe in accordance with the above-described RFLP methods. By comparing the RFLP pattern of the TIGR gene obtained from normal and glaucomatous patients, one can determine a patient's predisposition to glaucoma. The polymorphism obtained in this approach can then be cloned to identify the mutation at the coding region which alters the protein's structure or regulatory region of the gene which affects its expression level. Changes involving promoter interactions with other regulatory proteins can be identified by, for example, gel shift assays using HTM cell extracts, fluid from the anterior chamber of the eye, serum, etc. Interactions of TIGR protein in glaucomatous cell extracts, fluid from the anterior chamber of the eye, serum, etc. can be compared to control samples to thereby identify changes in those properties of TIGR that relate to the pathogenesis of glaucoma.

Several different classes of polymorphisms may be identified through such methods. Examples of such classes include: (1) polymorphisms present in the TIGR cDNA of different individuals; (2) polymorphisms in non-translated TIGR gene sequences, including the promoter or other regulatory regions of the TIGR gene; (3) polymorphisms in genes whose products interact with TIGR regulatory sequences; (4) polymorphisms in gene sequences whose products interact with the TIGR protein, or to which the TIGR protein binds.

In an alternate sub-embodiment, the evaluation is conducted using oligonucleotide "probes" whose sequence is complementary to that of a portion of TIGR mRNA. Such molecules are then incubated with cell extracts of a patient under conditions sufficient to permit nucleic acid hybridization. For this sub-embodiment, cells of the trabecular meshworks are preferred. The detection of double-stranded probe-mRNA hybrid molecules is indicative of the presence of TIGR mRNA; the amount of such hybrid formed is proportional to the amount of TIGR mRNA. Thus, such probes may be used to ascertain the level and extent of TIGR mRNA production in a patient's cells. Such nucleic acid hybridization may be conducted under quantitative conditions (thereby providing a numerical value of the amount of TIGR mRNA present). Alternatively, the assay may be conducted as a qualitative assay that indicates either that TIGR mRNA is present, or that its level exceeds a user set, predefined value.

In a second embodiment, the above-described "anti-TIGR antibodies" are employed in an immunodiagnostic assay for glaucoma and its related diseases.

As discussed above, TIGR protein is secreted into the extracellular matrix of the trabecular meshwork, and thus may circulate systemically in body fluids. This characteristic permits one to assay TIGR concentrations in blood, lymph, or serum, and to thereby determine whether a patient's TIGR levels exceed those found in the blood of individuals who are not suffering from glaucoma. Patients found to have abnormally high levels of TIGR thus may be diagnosed as glaucoma.

The anti-TIGR antibodies of the present invention may thus be used in an immunoassay to assess the presence of TIGR. Any of a wide array of immunoassays formats may be used for this purpose (Fackrell, *J. Clin. Immunoassay* 8:213–219 (1985)), Yolken, R. H., *Rev. Infect. Dis.* 4:35 (1982); Collins, W. P., In: *Alternative Immunoassays*, John Wiley & Sons, N.Y. (1985); Ngo, T. T. et al., In: *Enzyme Mediated Immunoassay*, Plenum Press, N.Y. (1985)).

The simplest immunoassay involves merely incubating an antibody that is capable of binding to a predetermined target molecule with a sample suspected to contain the target molecule. The presence of the target molecule is determined by the presence, and proportional to the concentration, of any antibody bound to the target molecule. In order to facilitate the separation of target-bound antibody from the unbound antibody initially present, a solid phase is typically employed. Thus, for example the sample can be passively bound to a solid support, and, after incubation with the antibody, the support can be washed to remove any unbound antibody.

In more sophisticated immunoassays, the concentration of the target molecule is determined by binding the antibody to a support, and then permitting the support to be in contact with a sample suspected of containing the target molecule. Target molecules that have become bound to the immobilized antibody can be detected in any of a variety of ways. For example, the support can be incubated in the presence of a labeled, second antibody that is capable of binding to a second epitope of the target molecule. Immobilization of the labeled antibody on the support thus requires the presence of the target, and is proportional to the concentration of the target in the sample. In an alternative assay, the target is incubated with the sample and with a known amount of labeled target. The presence of target molecule in the sample competes with the labeled target molecules for antibody binding sites. Thus, the amount of labeled target molecules that are able to bind the antibody is inversely proportional to the concentration of target molecule in the sample.

In general, immunoassay formats employ either radioactive labels ("RIAs") or enzyme labels ("ELISAs"). RIAs have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. RIAs are described in *Laboratory Techniques and Biochemistry in Molecular Biology*, by Work, T. S., et al., North Holland Publishing Company, N.Y. (1978), with particular reference to the chapter entitled "An Introduction to Radioimmune Assay and Related Techniques" by Chard, T., incorporated by reference herein. ELISAs have the advantage that they can be conducted using inexpensive equipment, and with a myriad of different enzymes, such that a large number of detection strategies—colorimetric, pH, gas evolution, etc.— can be used to quantitate the assay. In addition, the enzyme reagents have relatively long shelf-lives, and lack the risk of radiation contamination that attends to RIA use. ELISAs are described in *ELISA and Other Solid Phase Immunoassays* (Kemeny, D. M. et al., Eds.), John Wiley & Sons, N.Y. (1988), incorporated by reference herein.

In an alternative diagnostic format, ocular tissue (obtained, for example by trabeculotomy) may be evaluated in an in situ immunodiagnostic assay for glaucoma and its related diseases.

In such a format, antibodies (especially labeled antibodies) or other TIGR-binding peptides are incubated in the presence of ocular tissue in order to evaluate the clinical degree and significance of glaucoma in biopsied tissue. The extent, location, or degree of TIGR in the ocular tissue is determined by staining or other visualization methods. Such information is then compared to the staining pattern obtained from normal or glaucomatous individuals in order to diagnose glaucoma.

Anti-TIGR antibodies or TIGR binding molecules may be administered to a patient, and their capacity to bind to TIGR in vivo may be determined by ocular examination. Significantly, since such a diagnostic test is relatively rapid, immune responses that require significant time, such as the potential eliciting of anti-[anti-TIGR] antibodies, or the complexing of such antibodies with anti-TIGR antibodies is of not important. In a preferred embodiment, the antibody will be fluorescently labeled, and will be provided to a patient by injection into the patient's circulatory system. The antibody progresses from the circulatory system to the posterior optic chamber. The complexing of the antibody with TIGR can be monitored using conventional gonioscopy, or by other suitable means. Significantly, such an assay provides both a means to visualize the trabecular meshwork and a means for determining the extent of deposited TIGR in the extracellular matrix.

As discussed above, TIGR protein exhibits an ability to self-aggregate, due at least in part to the presence of leucine zippers in the molecule. Because small peptide fragments of TIGR that possess such zipper regions can bind to TIGR, such peptides may be used as alternatives to anti-TIGR antibodies in diagnostic assays. The use of such peptides is desirable since the peptides can be modified to possess both lipophilic and hydrophilic groups. The presence of such groups will permit the peptide to traverse the corneal membrane. Thus, such agents may be provided topically in an eye drop or ointment, and can be used in the same manner as anti-TIGR antibodies to effect the diagnosis of glaucoma. The peptide will desirably be labeled with a fluorescent group to facilitate detection.

Any suitable peptide fragment of TIGR may be used for this purpose, however, it is preferable to use a fragment corresponding to all or part of SEQ ID NO:1 residues 85–92, 92–99, 121–128; 128–135, 135–142, 142–149, 149–156, 241–248 and 374–381. Suitable lipophilic and hydrophilic groups are known in the art (see, Remington's Pharmaceutical Sciences), and comprise aliphatic groups, lipids, etc. (lipophilic groups) and organic acids, esters, ionic groups, etc. (hydrophilic groups). Such groups can be readily added to the TIGR molecules of the present invention by, for example, derivatizing the side chain groups of appropriate amino acids.

Cysteinyl residues may be reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues may be reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues may be converted to asparaginyl and glutaminyl residues by reaction with ammonium ions.

IV. Methods of Administration

The agents of the present invention can be formulated according to known methods to prepare pharmacologically acceptable compositions, whereby these materials, or their functional derivatives, having the desired degree of purity are combined in admixture with a physiologically acceptable carrier, excipient, or stabilizer. Such materials are non-toxic to recipients at the dosages and concentrations employed. The active component of such compositions may be TIGR protein, TIGR fusion proteins or fragments of TIGR protein or analogs or mimetics of such molecules. Where nucleic acid molecules are employed, such molecules may be sense, antisense or triplex oligonucleotides of the TIGR cDNA or gene.

A composition is said to be "pharmacologically acceptable" if its administration can be tolerated by a recipient patient. An agent is physiologically significant if its presence results in a detectable change in the physiology of a recipient patient.

Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)).

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween, Pluronics, or PEG, e.g., Tween 80, in an amount of, for example, 0.04–0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinyl pyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved through the use of polymers to complex or absorb the TIGR molecule(s) of the composition. The controlled delivery may be exercised by selecting appropriate macromolecules (for example polyesters, polyamino acids, polyvinyl pyrrolidone, ethylenevinylacetate, methylcellulose, carboxymethylcellulose, or protamine sulfate) and the concentration of macromolecules as well as the methods of incorporation in order to control release.

Sustained release formulations may also be prepared, and include the formation of microcapsular particles and implantable articles. For preparing sustained-release compositions, the TIGR molecule(s) of the composition is preferably incorporated into a biodegradable matrix or microcapsule. A suitable material for this purpose is a polylactide, although other polymers of poly-(α-hydroxycarboxylic acids), such as poly-D-(−)-3-hydroxybutyric acid (EP 133,988A), can be used. Other biodegradable polymers include poly(lactones), poly (orthoesters), polyamino acids, hydrogels, or poly (orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Patent No. 1176565, Sidman, U. et al., *Biopolymers* 22:547 (1983), and Langer, R. et al, *Chem. Tech.* 12:98 (1982).

Alternatively, instead of incorporating the TIGR molecule (s) of the composition into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In an alternative embodiment, liposome formulations and methods that permit intracellular uptake of the molecule will be employed. Suitable methods are known in the art, see, for example, Chicz, R. M. et al. (PCT Application WO 94/04557), Jaysena, S. D. et al. (PCT Application WO93/12234), Yarosh, D. B. (U.S. Pat. No. 5,190,762), Callahan, M. V. et al. (U.S. Pat. No. 5,270,052) and Gonzalezro, R. J. (PCT Application 91/05771), all herein incorporated by reference.

The pharmaceutical compositions of the present invention may be sterilized, as by filtration through sterile filtration membranes (e.g., 0.2 micron membranes). The compositions may be stored in lyophilized form or as a liquid solution. It will be understood that use of certain of the foregoing excipients, carriers, or stabilizers will result in the formation of salts of the molecules.

The compositions of the present invention can be applied topically as to the skin, or to the cornea. When applied topically, the molecule(s) of the composition may be suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, and bandages, preferably in liquid or semi-liquid form.

For obtaining a gel formulation, the molecule(s) of the composition formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, non-toxic, simple to prepare, and not too runny or viscous, and will not destabilize the TIGR molecule(s) held within it. Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The compositions of the present invention can also be formulated for administration parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers, adjuncts or occlusive dressings can be used to increase tissue permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents.

If methylcellulose is employed in the gel, preferably it comprises about 2–5%, more preferably about 3%, of the gel and the TIGR molecule(s) of the composition is present in an amount of about 300–1000 $\mu$g per ml of gel. The dosage to be employed is dependent upon the factors described above. As a general proposition, the TIGR molecule(s) of the composition is formulated and delivered to the target site or tissue at a dosage capable of establishing in the tissue a maximum dose that is efficacious but not unduly toxic.

In the most preferred embodiment, the molecules of the invention will be provided to the cornea or surface of the eye, and permitted to adsorb across the cornea into the anterior chamber of the eye. Methods that may be used for accomplishing such ocular drug delivery are described by Zun, L. S. (*Emerg. Med. Clin. North. Amer.* 6:121 (1988)), Lee, V. H. (*J. Ocular Pharmacol.* 6:157 (1990)), Ellis, P. P. (In: *Ocular Therapeutics and Pharmacology*, 7th ed., Mosby, (1987)) and (Vaughan, D. et al., In: *General Ophthamology*, Appleton & Lange, Norwalk, Conn., pp. 213–230 (1992)).

Most preferably, however, such drug administration will be accomplished by combining effective amounts of the agents of the invention with any of the sustained release ophthalmic delivery systems described by Davis, J. P. et al. (U.S. Pat. No. 5,192,535, herein incorporated by reference).

Such preferred sustained release topical ophthalmic medicament delivery systems comprise an aqueous suspension at a pH of from about 3 to about 6.5 and an osmotic pressure of from about 10 to about 400 mOsM containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a crosslinking agent, such weight percentages of monomers being based on the total weight of monomers polymerized. Desirably the polymer is prepared by suspension or emulsion polymerizing the monomer with the crosslinking agent to a particle size of not more than about 50 µm, preferably not more than about 30 µm, in equivalent spherical diameter. The suspension has an initial viscosity of from about 1,000 to about 30,000 centipoises (cp) and is administrable to the eye in drop form at that initial viscosity. The polymer has average particle size of not more than about 50 µm, preferably not more than about 30 µm, in equivalent spherical diameter. In general, such polymers will range in molecular weight estimated to be about 250,000 to about 4,000,000, and preferably about 500,000 to about 2,000,000.

Aqueous suspensions containing polymer particles prepared by suspension or emulsion polymerization whose average dry particle size is appreciably larger than about 50 µm in equivalent spherical diameter are less comfortable when administered to the eye than suspensions otherwise identical in composition containing polymer particles whose equivalent spherical diameters are, on the average, below about 50 µm. Moreover, above the average 50 µm size, the advantage of substantially increased viscosity after administration is not realized.

The lightly crosslinked suspension is administrable in drop form, upon contact of the lower pH suspension with the higher pH tear fluid of the eye, the suspension is rapidly gellable to a substantially greater viscosity than the viscosity of the suspension as originally administered in drop form. Accordingly, the resulting more viscous gel can remain in the eye for a prolonged period of time so as to release.

The polymer of the preferred intra-ocular drug delivery system is preferably prepared from at least about 50% by weight, more preferably at least about 90% by weight, of one or more carboxyl-containing monoethylenically unsaturated monomers. Acrylic acid is the preferred carboxyl-containing, monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), p-hydroxycoumaric acid (umbellic acid), and the like can be used in addition to or instead of acrylic acid.

Such polymers are crosslinked by using a small percentage, i.e., less than about 5%, such as from about 0.5% or from about 0.1% to about 5%, and preferably from about 0.2% to about 1%, based on the total weight of monomers present, of a polyfunctional crosslinking agent. The crosslinking agents of such compositions include non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. A preferred crosslinking agent is divinyl glycol. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown, U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products, and reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250.

In a preferred method of preparing sustained release topical ophthalmic delivery systems, the foregoing suspensions are prepared and packaged at the desired viscosity of from 1,000 to about 30,000 centipoises, for administration to the eye in drop form. In a preferred delivery method, the foregoing suspensions, containing the medicament, are administered to the eye at the initial viscosity in drop form to cause the administered suspension, upon contact with the higher pH tear fluid of the eye, to rapidly gel in situ to a substantially greater viscosity than the viscosity of the suspension as originally administered in drop form. The more viscous gel remains in the eye for a prolonged period of time so as to release the medicament, entrapped in the more viscous gel formed in the eye, in sustained fashion.

It may be desirable to replace up to about 40% by weight of the carboxyl-containing monoethylenically unsaturated monomers by one or more non-carboxyl-containing monoethylenically unsaturated monomers containing only physiologically and ophthamologically innocuous substituents.

The desired osmotic pressure is preferably achieved by using a physiologically and ophthalmologically acceptable salt in an amount of from about 0.01% to about 1% by weight, based on the total weight of the suspensions. A preferred salt is sodium chloride.

Generally, the dosage needed to provide an effective amount of the composition will vary depending upon such factors as the recipient's age, condition, sex, and extent of disease, if any, and other variables, and can be adjusted and determined by one of ordinary skill in the art. Effective amounts of the compositions of the invention can vary from 0.01–1,000 mg/ml per dose or application, although lesser or greater amounts can be used. For ophthalmic suspensions, the effective amounts will preferably be from about 0.005% to about 10% by weight, and most preferably from about 0.01% to about 5% by weight, based on the total weight of the suspension.

Having now generally described the invention, the same will be more readily understood through reference to the following examples which are provided by way of illustration, and are not intended to be limiting of the present invention, unless specified.

EXAMPLE 1

CLONING OF TIGR cDNA

In order to clone the major DEX-inducible cDNA of HTM cells, a subtraction screening procedure was employed. In such subtractive screening methods, cDNA molecules created from a complete population of cells are permitted to hybridize with a cDNA library constructed from RNA of different subpopulations of cells in order to identify clones that exhibit differential expression, and that thus reflect mRNA molecules that are induced or repressed in each population (Lamar, E. E. et al., *Cell* 37:171–177 (1984); Rubenstein, J. L. R. et al., *Nucleic Acids Res.* 18:4833–4842 (1990); Hedrik, S. M. et al., *Science* 308:149–153 (1984); Duguid, J. R. et al., *Proc. Natl. Acad. Sci. (U.S.A.)* 85:5738–5742 (1988); Weiland, I. et al., *Proc. Natl. Acad. Sci. (U.S.A.)* 87:2720–2724 (1990)).

cDNA was therefore prepared from mRNA of human trabecular meshwork (HTM) cells that had been incubated in 100 nM dexamethasone for 10 days, as well as from mRNA of untreated HTM cells. The cDNA library was constructed in lambda ZapII using strain XL-1 (Stratagene, San Diego). Approximately 30–50 μg of mRNA were obtained from 5×10⁷ dexamethasone treated cells as described by Nguyen, T. D. et al. (In: "*Schriftenreihe de Adademie der Wissenschaften und der Literatur, Mainz,*" 331–343 (1993), herein incorporated by reference).

Two independent screenings of 20,000 phages each were conducted using a differential screening approach. Phages were separately probed with labeled cDNA made from mRNA of untreated cells and of dexamethasone-treated cells for 1 day and 10 days. Clones that exhibited an inducible response (i.e. increased labeling when probed with the dexamethasone treated cDNA relative to control cDNA) were desired candidates for further analysis.

Several cDNA clones were obtained that corresponded to mRNA produced in higher amounts in dexamethasone-treated cells. One cDNA clone, corresponding to mRNA that was present in the dexamethasone-treated cells, but absent from the untreated cells, was designated "clone II.2" or "TIGR" (T. D. Nguyen et al., *Invest. Ophthalmol. Vis. Sci.* 32:789 (1991)). A second clone encoded alpha-1 antichymotrypsin.

The level of these changes was quantitated by both dot-blot and PCR methodology. In the dot-blot analysis, the DNA of the clones are serially diluted and applied to membranes which are then hybridized to labeled total cDNA of control, 1 day or 10 day dexamethasone-treated HTM cells. The dot-blot analysis revealed that the TIGR mRNA was the major induced species, comprising 3–4% of the total cellular mRNA at day 10. An insignificant level of TIGR mRNA was detected in the control. The time course of dexamethasone treatment for days 2, 4, 7 and 10 revealed that TIGR was progressively induced (T. D. Nguyen et al., *Invest. Ophthalmol. Vis. Sci.* 32:789 (1991)). Cycloheximide studies showed that the induction required protein synthesis. Southern analysis and in-situ hybridization show multiple copy numbers of the gene. For PCR amplification analysis, the serial dilution PCR method (Chelly, J. D. et al., *Eur. J. Biochem.* 187:691–698 (1990); Murphy, L. D. et al., *Biochem.* 29:10350–10356 (1990); Singer-Sam, J. O. et al., *Nucl. Acids Res.* 18:1255–1259 (1990)) was modified to maintain the exponential range of the amplification throughout the quantitation procedure to meaure and confirm the major and progressive induction of TIGR mRNA over a 10 day dexamethasone induction period. Quantitative PCR analysis revealed an induction level of about 20 fold compared to the level found in cells that had been treated with dexamethasone for only 1 day.

Northern analysis showed clone TIGR to be approximately 2.5 kb, and to encode a protein of unique sequence. The induction of the mRNA required protein synthesis and insulin-like growth factor reduced the induction effect by 50%. The TIGR mRNA induction was not observed in dexamethasone treated fibroblasts, keratinocytes, or ciliary epithelial cells. The pattern of induction in HTM cells was distinguishable from other steroid induced proteins such as metallothionine, alpha$_1$-acid glycoprotein, and TAT which were maximally induced by one day dexamethasone treatment. In addition to dexamethasone, the TIGR mRNA was induced in HTM cells exposed to hydrogen peroxide, TPA, or glucose for 3–24 hours. Dexamethasone treatment produced substantial loss in the mRNAs for glucocorticoid receptors and heat shock proteins (e.g., hsp 90 mRNA levels fell approximately 20 fold after 10 days of dexamethasone treatment).

EXAMPLE 2

EXPRESSION OF TIGR

An ability to express substantial amounts of TIGR would facilitate the use of this protein for functional assays, and the development of anti-TIGR antibodies. To achieve such enhanced expression, the PVL1393 baculovirus transfer vector of Invitrogen Corp. was employed. A 2 Kb Eco-R1 fragment of the TIGR cDNA was inserted into the Eco R1 cloning site of (2 Kb Eco-R1/PVL 1393 was deposited on Jul. 15, 1997 with the American Type Culture Collection, 10801 University Boulevard, Manassas, Va. 20110-2209. PCR and sequencing analysis showed that the insert had been ligated in the correct orientation into the vector's polyhedrin promoter. Cotransfection of this construct and wild type baculovirus DNA into Sf9 insect cells produced high titers of recombinant protein. The Sf9 insect cell line can be obtained from the American Type Culture Collection, Rockville, Md., US, as deposit accession number ATCC CRL 1711. Methods of using such vectors and cells are described by Summers M. D. et al. (In: *A Manual of Methods for Baculovirus Vectors and Insect Cell Culture Procedures*, Texas Agricultural Experiment Station Bulletin No. 1555 (1987)), and Summers, M. D. (U.S. Pat. No. 5,278,050).

PCR verification of these recombinants showed positive signal for the expressed gene. SDS gel analysis of the SF9 transfected cellular proteins showed that the new product had a molecular weight of about 55 KDa and amounted to 90–95% of the total protein produced. These values correlated well with the size of the HTM cell protein induced by dexamethasone (DEX) (Polansky, J. R. et al., *Prog Clin Biol Res* 312:113–138, 1989) and the calculated MW from the cDNA sequence isolated. G-150 (Pharmacia) column purification and Edman degradation sequencing of the protein confirmed the open reading frame of the TIGR cDNA.

Studies of the recombinant protein thus suggested (1) that the 55 kD protein existed both in cells and in the medium, (2) that it underwent oligomerization, (3) phosphorylation, (4) glycosylation, (5) that it was susceptable to metalloprotease, (6) that it exhibited high affinity binding to extracellular matrix and human trabecular meshwork cells, (7) that it exhibited progressive inductions with time in both cell and organ cultures, and (8) that it exhibited high expression in the HTM of glaucomatous patients as compared to normal patients. Significantly, the induction correlated with topical glucocorticoid effects on intra-ocular pressure in patients, and differed from other known glucocorticoid induction patterns which exhibit close to maximal induction at only one day of dexamethasone treatment.

EXAMPLE 3

STRUCTURAL CHARACTERISTICS OF TIGR

Clone TIGR was sequenced, and found to comprise a 2.0 kb cDNA molecule (SEQ ID NO:2). The full-length transcript was nearly 2.5 kb as determined by Northern analysis. The cDNA included two ATG start sites which produced two 55 kD proteins in both HTM and Sf9 cells. The larger protein is 497 amino acids, and is defined by the TIGR open reading frame (SEQ ID NO:1). The larger protein is due to the unprocessed form of TIGR; the smaller protein reflects the proteolytic cleavage of the TIGR signal peptide. The amino terminal sequence of these proteins has been verified by amino acid sequencing analysis. The post-translational modification of these proteins also produced a highly glycosylated TIGR form og about 66 kD.

Structural analysis of the clone demonstrated it encoded a novel extracellular protein of about 55 kD with an N-glycosylation site at SEQ ID NO:1 residues 57–60 and O-glycosylation sites at SEQ ID NO:1 residues 221–222; 222–223; 270–272; 305–306; 397–401; 453–457; 457–459, heparin sulfate binding (SEQ ID NO:1 residues 110–113 and 146–150) and initiation domains (SEQ ID NO:1 residues 223–224, 231–232 and 324–325 ), 7 consensus leucine zipper units, forming two stretches, one located at SEQ ID NO:1, residues 85–92 and 92–99, and five located at SEQ ID NO:1, residues 121–128; 128–135; 135–142; 142–149; and 149–156), and a potential GIP (guanidyl inositol phosphate) linkage. The 55 kD recombinant protein forms dimer or heteromer in the HTM medium as demonstrated by crosslinking studies, and it could self-aggregate. The recombinant protein had a specific ability to bind trabecular meshwork cells ($4.3 \times 10^{-9}$M and $2.3 \times 10^{-8}$M) as shown by Skatchard analysis. In contrast, the protein showed non-saturable and low affinity binding ability for fibroblasts. The recombinant protein was shown to be a substrate for the 72 kD metalloprotease.

The anti-TIGR antibodies recognize a 66 kD protein in DEX-treated HTM medium. This protein was shown to be a highly glycosylated form of the 55 kD TIGR protein. This conclusion was supported by the observation that expression conducted in the presence of tunicamycin shifted production from 66 kD to 55 kD. The 66 kD glycosylated form of TIGR appears to be a hyaluronate binding protein, since it was found to be capable of binding to hyaluronic acid beads. Such binding proteins are defined by their ability to bind to such beads and to be eluted from the beads in the presence of 4M guanidine after 0.15 and 1.5M NaCl washes.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

What is claimed is:

1. A substantially purified human Trabecular Meshwork Induced Glucocorticoid Response (TIGR) nucleic acid molecule which comprises an oligonucleotide fragment between about 15 to about 250 nucleotides of the sequence of SEQ ID NO:3.

2. An isolated human Trabecular Meshwork Induced Glucocorticoid Response (TIGR) nucleic acid molecule which comprises an oligonucleotide fragment between about 15 to about 250 nucleotides of the sequence of SEQ ID NO:3.

3. A substantially purified mammalian Trabecular Meshwork Induced Glucocorticoid Response (TIGR) nucleic acid molecule which comprises an oligonucleotide fragment between about 15 to about 250 nucleotides of the sequence of SEQ ID NO:3 or its complement that specifically hybridizes with a polynucleotide of the sequence of SEQ ID NO:3 or its complement.

4. An isolated mammalian Trabecular Meshwork Induced Glucocorticoid Response (TIGR) nucleic acid molecule which comprises an oligonucleotide fragment between about 15 to about 250 nucleotides of the sequence of SEQ ID NO:3 or its complement that specifically hybridizes with a polynucleotide of the sequence of SEQ ID NO:3 or its complement.

5. A substantially purified human Trabecular Meshwork Induced Glucocorticoid Response (TIGR) nucleic acid molecule which comprises an oligonucleotide fragment between about 15 to about 250 nucleotides of the sequence of SEQ ID NO:3 or its complement that specifically hybridizes with a polynucleotide of the sequence of SEQ ID NO:3 or its complement.

6. An isolated human Trabecular Meshwork Induced Glucocorticoid Response (TIGR) nucleic acid molecule which comprises an oligonucleotide fragment between about 15 to about 250 nucleotides of the sequence of SEQ ID NO:3 or its complement that specifically hybridizes with a polynucleotide of the sequence of SEQ ID NO:3 or its complement.

* * * * *